United States Patent
Liu et al.

(10) Patent No.: US 6,431,014 B1
(45) Date of Patent: Aug. 13, 2002

(54) HIGH ACCURACY AEROSOL IMPACTOR AND MONITOR

(75) Inventors: Benjamin Y. H. Liu, North Oaks; Virgil A. Marple, Maple Plain, both of MN (US)

(73) Assignee: MSP Corporation, Minneapolis, MN (US)

( * ) Notice: Subject to any disclaimer, the term of this patent is extended or adjusted under 35 U.S.C. 154(b) by 0 days.

(21) Appl. No.: 09/360,466

(22) Filed: Jul. 23, 1999

(51) Int. Cl.[7] ............................. G01N 1/24; G01N 15/02
(52) U.S. Cl. ................. 73/863.22; 73/28.05; 73/863.03
(58) Field of Search ......................... 73/863.22, 863.02, 73/863.03, 28.05, 28.06, 864.34, 865.5

(56) References Cited

U.S. PATENT DOCUMENTS

| | | | | |
|---|---|---|---|---|
| 2,538,116 A | | 1/1951 | May ........................ 73/28.04 |
| 3,001,914 A | * | 9/1961 | Anderson ............... 73/28.05 X |
| 3,127,763 A | | 4/1964 | Lippman .................. 73/28.06 |
| 3,518,815 A | | 7/1970 | McFarland et al. ....... 73/863.22 |
| 3,693,457 A | | 9/1972 | Pilat ........................ 73/865.5 |
| 3,901,798 A | * | 8/1975 | Peterson ................ 73/865.5 X |
| 3,922,905 A | * | 12/1975 | Roth ........................ 73/28.04 |
| 4,133,202 A | | 1/1979 | Marple .................... 73/28.06 |
| 4,189,937 A | * | 2/1980 | Nelson ..................... 73/28.06 |
| 4,211,116 A | * | 7/1980 | Pilat et al. ................ 73/863.22 |
| 4,321,822 A | | 3/1982 | Marple et al. .......... 73/863.22 |
| 4,387,603 A | * | 6/1983 | Nelson .................... 73/863.22 |
| 4,391,151 A | | 7/1983 | Nelson et al. ........... 73/863.23 |
| 4,400,982 A | | 8/1983 | Belle ....................... 73/863.22 |
| 4,452,068 A | | 6/1984 | Loo ......................... 73/28.05 |
| 4,463,595 A | | 8/1984 | Yeh et al. ............. 73/863.33 X |
| 4,554,051 A | * | 11/1985 | Danforth ............... 73/53.04 X |
| 4,570,494 A | | 2/1986 | Dunn et al. ............. 73/863.22 |
| 4,640,140 A | | 2/1987 | Burghoffer et al. ...... 73/863.22 |
| 4,725,294 A | | 2/1988 | Berger ................. 73/863.22 X |
| 4,764,186 A | | 8/1988 | Langer ........................ 95/268 |
| 4,827,779 A | | 5/1989 | Marple et al. ........... 73/863.22 |
| 4,972,957 A | | 11/1990 | Liu et al. ..................... 209/143 |
| 5,201,231 A | | 4/1993 | Smith ....................... 73/863.22 |
| 5,323,657 A | * | 6/1994 | Vander Heyden .... 73/863.03 X |
| 5,343,767 A | | 9/1994 | Marple et al. ........... 73/863.22 |
| 5,437,198 A | | 8/1995 | John ....................... 73/863.22 |
| 5,693,895 A | | 12/1997 | Baxter ..................... 73/863.22 |

FOREIGN PATENT DOCUMENTS

RU          840707    *  6/1981    ................. 73/28.05

* cited by examiner

*Primary Examiner*—Thomas P. Noland
(74) *Attorney, Agent, or Firm*—Westman, Champlin & Kelly, P.A.

(57) ABSTRACT

An aerosol impactor and monitor has a plurality of impactor stages, each of which will receive an aerosol and classify the aerosol according to particle size. The impactor stages have nozzle plates and impaction plates that reduce the effects of cross flow under high flow volumes, as well as including monitors for determining pressure drop to permit analyzation of performance of the impactors. The impaction plates are mounted so that they can be rotated within the separate impactor chambers through the use of magnetic attraction drives to eliminate the need for rotating seals and yet obtain the benefit of the rotatable impaction plates. Pressure sensors are used for determining pressure drop across nozzle plates, both to insure evaluation of the flow rate through the impactor and also to determine the condition of the nozzles.

13 Claims, 10 Drawing Sheets

HIGH ACCURACY AEROSOL IMPACTOR AND MONITOR

BACKGROUND OF THE INVENTION

This invention relates to a cascade aerosol impactor for classifying aerosol particles that includes pressure sensors for monitoring the functions of the impactor, and further includes mounting structure that permits rotating impaction plates without mechanical drives that require seals. The nozzles used are also constructed to reduce cross flow effects.

Inertial impactors are widely used for measuring the size distribution of aerosols. For purpose of this invention, particles suspended in a gas are referred to as an aerosol. The gas is usually air, but other gases such as nitrogen, oxygen, argon, helium, etc. can also be the suspending gaseous medium. The particles can be a solid, a liquid, or a mixture of both. The particle size is usually between 0.002 $\mu$m and 100 $\mu$m.

Inertial impactor, aerosol impactor, or impactor all refer to an aerosol sampling or collection device that separates aerosol particles from the gaseous medium in which they are suspended by the inertial effect of the particles. The device usually uses a nozzle to accelerate the gas to a high velocity and direct the gas jet against an impaction plate to cause particle impaction on the plate. Particles will impact only when their size is larger than a certain critical value, while smaller particles with insufficient momentum or inertia will be carried by the gas flow around the plate to an exit and escape collection.

The critical particle size at which particle collection occurs is referred to as the impactor cut-point. The cut-point particle diameter of an impactor can be varied by varying the nozzle size and gas velocity. Smaller nozzles and higher gas velocities will produce smaller cut-point particle diameters. The impactor cut-point is also affected by the gas viscosity, the shape of the nozzle, as well as the nozzle-to-plate distance. In an ideal impactor all particles larger than the cut-point are collected with 100% efficiency while smaller particles are not collected. In a real impactor, particle impaction does not occur ideally at a single particle size. The transition from zero to 100% particle collection usually occurs over a range of particle sizes. The narrower this range, the sharper the impactor cut-size characteristics. The ideal impactor is then an impactor with a perfect cut value. In a real impactor with less than a perfect sharpness-of-cut, the cut-point is usually defined as the particle diameter at which 50% of the particles are collected.

Figure 1:
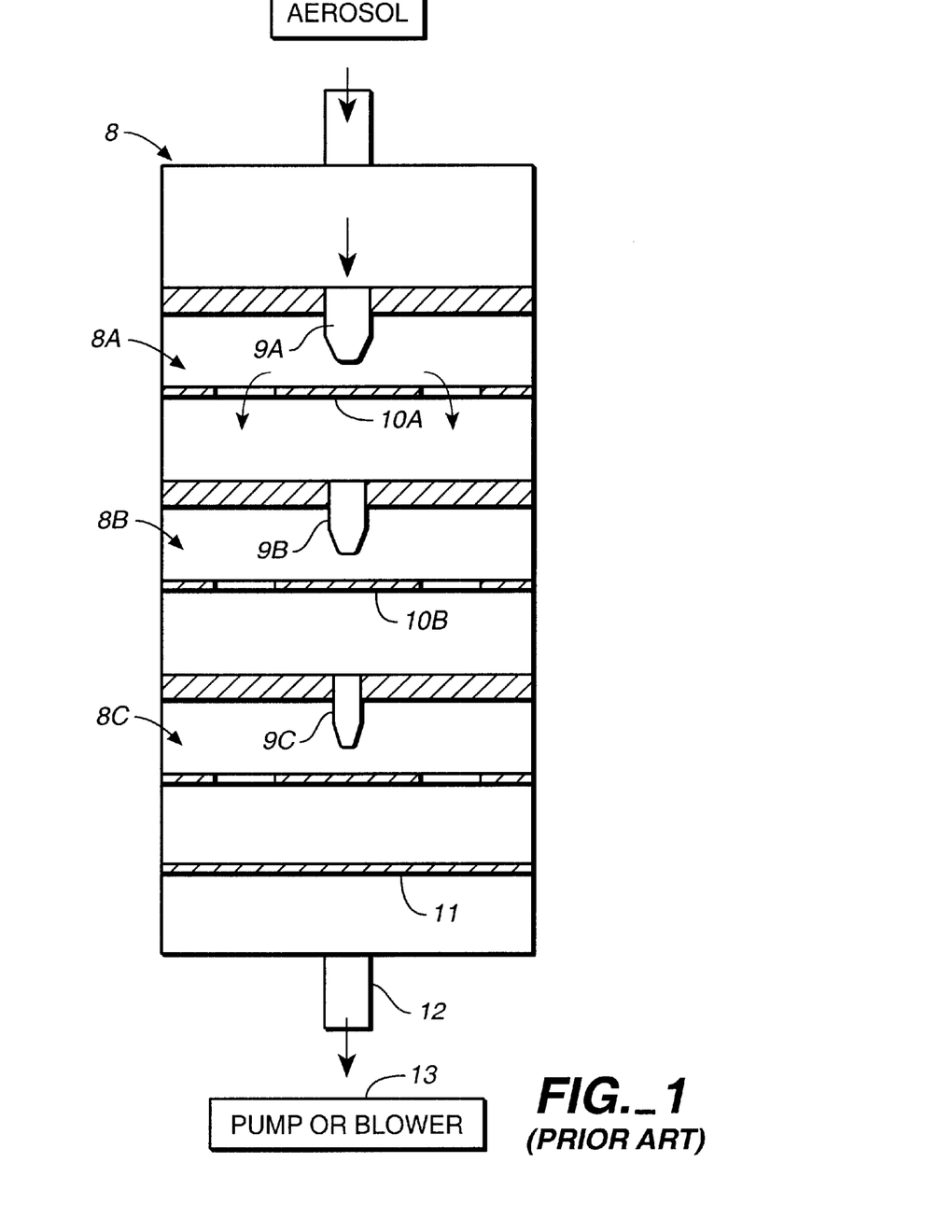

The prior art impactor just described is a single stage impactor. It consists of a single nozzle plate carrying one or more nozzles in parallel and an adjacent impaction plate. Several single-stage impactors can be arranged in series to form a cascade impactor. Cascade impactors are designed so that large particles are collected first, followed by smaller and smaller particles between an inlet and an outlet. There is usually a final filter to collect small particles below the cut-point of the last impactor stage. For instance, in a three-stage impactor with cut-point diameters of, say 10, 3 and 1 $\mu$m, particles larger than 10 $\mu$m are removed by the first, 10-$\mu$m cut stage. Subsequently, particles in the 3-to-10 $\mu$m and the 1-to-3 $\mu$m ranges are removed by the 3-$\mu$m and 1-$\mu$m cut stages, respectively. The final filter then collects particles smaller than 1 $\mu$m. FIG. 1 is a schematic diagram of a prior art three-stage impactor with a final filter, in which a single nozzle of a progressively smaller diameter is used in each stage to increase the gas velocity to higher and higher values to collect smaller and smaller particles.

The cascade impactor is very useful for size distribution analysis of aerosol particles. Particulate air pollutants, aerosols in the work place environment, as well as other aerosols of practical interest are usually polydisperse, with particle sizes spread over a wide range of values. Cascade impactors can be used to separate particles by size into narrower intervals for analysis. The size-fractionated particles can then be analyzed gravimetrically to determine their mass size distribution. Alternatively, the particles can be analyzed chemically to determine the chemical composition of the particles as a function of particle size. Cascade impactors are widely used in air pollution studies to determine the physical and chemical properties of the airborne particles, assess their potentially harmful health effect, or determine the origin of the particles for pollution abatement or control purposes.

In the schematic prior art diagram of FIG. 1, an aerosol source 6 is connected to an inlet of a cascade impactor 8. Impactor 8 has a single nozzle 9A, 9B and 9C in each impactor stage 8A, 8B and 8C. Impaction plates 10A, 10B and 10C are provided and a filter 11 follows impactor stage 8C. An outlet 12 leads to a pump or a blower 13. In practical impactors, each impactor stage is usually comprised of a number of nozzles formed in a nozzle plate. The flow through each nozzle can be quite small, but the total flow through all the nozzles can be quite high by using a large number of nozzles in parallel. A high sampling flow rate is needed to increase sample collection so that the quantity of particulate matter collected is sufficient for analysis.

In recent years, demands for increased accuracy and precision for aerosol measurement have led to the development of cascade impactors with a high volumetric flow rate and large number of impactor stages. For instance, the Micro-Orifice Uniform Deposit Impactor, sold under the trademark MOUDI™, manufactured by the MSP Corporation of Minneapolis, Minn., the assignee of this application, comprises eight (8) or ten (10) impactor stages with nominal cut-point particle diameters that range between 18, 10, 5.6, 3.2, 1.8, 1.0, 0.56, 0.32, 0.18, 0.1 and 0.056 $\mu$m. In the final stages, nozzle diameters as small as 50 $\mu$m are used. To provide the needed 30 liter-per-minute sampling flow rate, as many as 2,000 nozzles are used in some stages.

The need for increased measurement sensitivity in air pollution research and for other applications has created the need for impactors with flow rates larger than the 30 liters-per-minute. To design impactors with higher flow rates, even larger number of nozzles need to be used. To create a cascade impactor with, say, 90 liters-per-minute sampling flow rate, and similar operational pressure drop characteristics, the number of small nozzles needs to be increased by a factor of 3. Thus, 6000 nozzles need to be used in the final stages of such high flow MOUDI™ cascade impactors.

In designing impactors with large numbers of very small nozzles, it is important to consider the effect of cross flow in the impactor. As will be explained, when a nozzle plate with a large number of nozzles is provided, the gas flow through the outer nozzles, must pass radially outward across the surface of the nozzle plate between it and the impaction plate. This outward radial gas flow is referred to as the cross-flow. The cross flow can cause the gas jets through the nozzles in the cross flow path to be deflected side ways and change their cut-point characteristics. The sharpness-of-cut of the impactor as a whole will then decrease. The cross flow effect is the greatest for nozzles located near the outer edges of the nozzle cluster. To obtain good sharpness-of-cut characteristics, it is important to consider the cross flow effect in designing high flow impactors.

The use of large number of very small nozzles also creates the practical issue of nozzle plugging during use. As aerosols are sampled by the impactor, some accumulation of particulate matter around the edge of the nozzle is unavoidable. Over time, enough material can accumulate to partially block the flow and cause the cut-point of the impactor to change. This effect, if not monitored, can lead to measurement errors. The nozzles can usually be cleaned, but cleaning, if done improperly, for instance, by using a high intensity ultrasonic cleaner, can cause damage to the nozzle plate and alter the size of the nozzles.

Another issue relating to high accuracy, high precision modern impactor is that the use of a large number of impactor stages can cause errors in the assembly of the impactors. In the MOUDI™ system referred to above, eight and ten impactor stages are used. Usually, the impactor stages must be assembled with impactor stage cut-points in a decreasing order. If, due to an operator mistake, the impactor stages are assembled incorrectly with the order of some stages reversed, erroneous data will be collected. The present invention solves the problems outlined, including the reduction of cross flow, monitoring changes in cut point and automatically detecting errors in the assembly and use of cascade impactors.

SUMMARY OF THE INVENTION

The present invention relates to a cascade impactor that provides a very accurate particle size cutoff at each of the stages of the impactor. The particle sizes are obtained by precise controlling of cross flow, and also by monitoring the performance of the nozzle plate. Additionally, enhanced operation is achieved by rotating the impaction plates utilizing a drive, which avoids the need for rotating seals between individual stages of the impactor. By monitoring the pressure drop across the individual stages and comparing it with standard or reference values of pressure drop obtained for similar nozzle plates, or obtained by calibrating the nozzle plates, any changes that indicate leaks, damage to the nozzle plates, or other detrimental factors can be determined quickly. Further, monitoring pressure also insures a check that the assembly of the various stages of the impactor is appropriate, because errors in assembly will cause changes in the pressure drop across the nozzle plates at different stages. Preset limits of pressure drop change can be set so that when the different pressure changes reach the set amount, alarms or other indicators can be activated for alerting an operator to a problem.

In one form of the invention, an optical sensor is used for providing signals indicating amount s of an aerosol provided by a drug delivery device on order to provide automatic measurement of such aerosol.

The overall construction thus insures simple operation, simple assembly and reliable, accurate classification of particles at quite "sharp" cutoff points.

DEFINITION OF TERMS

For purpose of this invention, the various terms are defined as follows:

Aerosol: Aerosol means small particles suspended in a gas. The gas is usually air, but can also be nitrogen, oxygen, argon, and other types of gases. The particles can be solid, liquid or a mixture of both. The particle size is usually between 0.002 $

DETAILED DESCRIPTION OF THE ILLUSTRATIVE EMBODIMENTS

Figure 2:
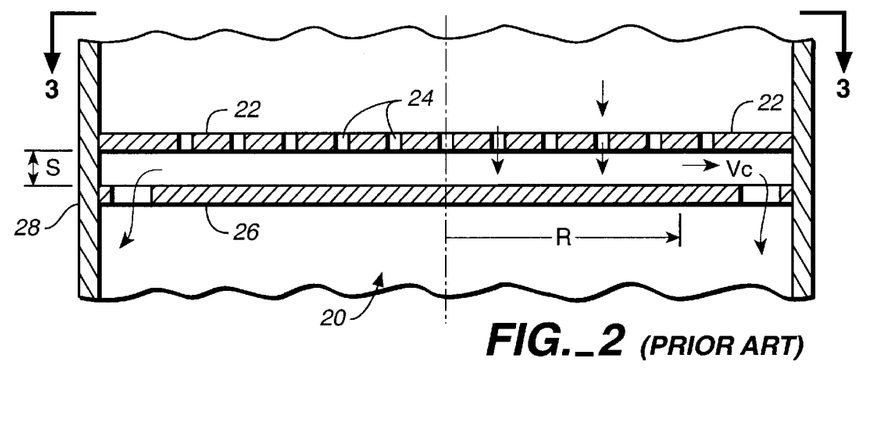
Figure 3:
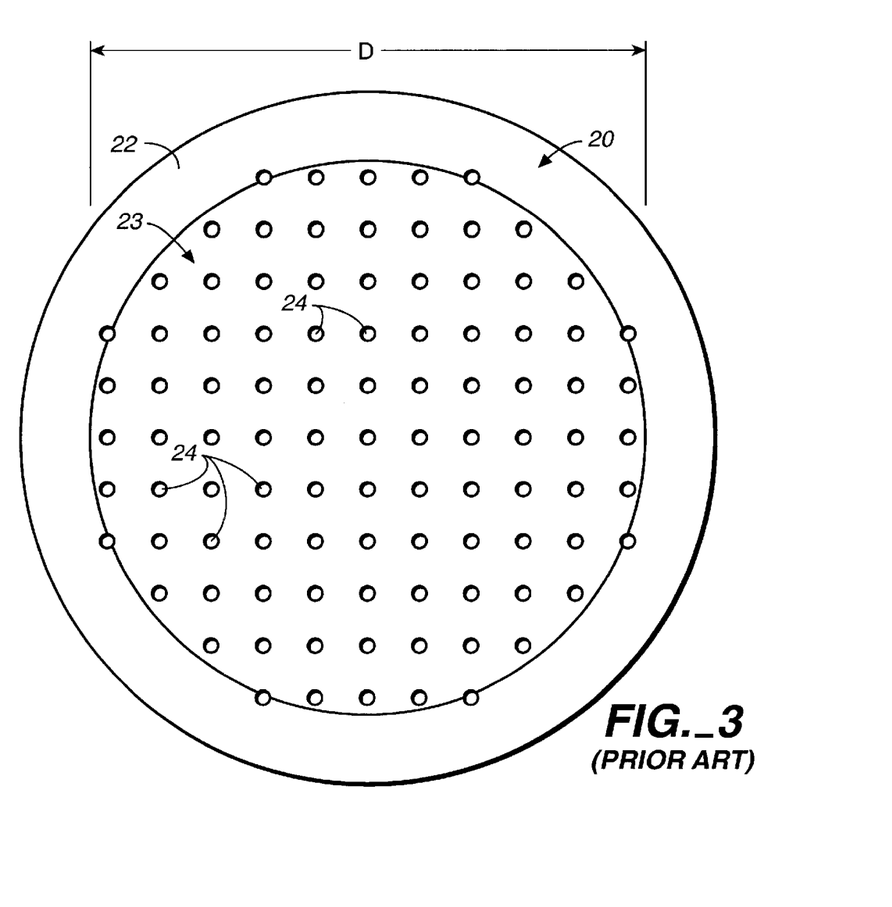

The schematic diagram of a single prior art impactor stage 20 shown in FIGS. 2 and 3 including a nozzle plate 22 having a cluster 23 of a multitude of nozzles 24 through the nozzle plate which is positioned upstream from an adjacent impaction plate 26. The impaction plate 26 and nozzle plate 22 are held in a housing 28, and are substantially parallel. The nozzles 24 are all located within the circular cluster area of diameter D and distributed uniformly over the area. With increased sampling flow rate and the use of a large number of nozzles 24, the diameter, D, of the nozzle cluster 23 must be increased. The higher flow also causes increased cross-flow as discussed earlier.

As illustrated in FIG. 2, nozzle plate 22 has N nozzles 24 distributed uniformly over a circular area of diameter, D, and impaction plate 26 is at a distance S from the nozzle plate 22. The gas flow through the nozzles 24 within the circular area of radius R is proportional to the number of nozzles within the circle. The flow on the upper surface of the impaction plate must pass radially outward across the perimeter of the circle, along the under surface of the nozzle plate. The outward radial gas flow is the cross-flow. The cross flow can cause the gas jets from the nozzles 24 in its path to be deflected side ways and change their cut-point characteristics. The sharpness-of-cut of the impactor as a whole will then decrease. As the radial distance, R, is increased from the center (R=0) to the edge (R =0.5 D), the cross flow, $Q_c$, is increased in proportion to $R^2$, and the cross-flow area, A=2×3.14 (R) (S), is increased in proportion to the radius, R. The cross flow velocity, $V_c$, which is equal to Q/A, thus increases in proportional to the radius, R. The cross flow velocity, and its potential effect, are thus zero for nozzles located at the center and the effect is the greatest for nozzles located near the outer edges of the nozzle cluster. To obtain good sharpness-of-cut characteristics, it is important to consider the cross flow effect in designing high flow impactors.

Figure 4:
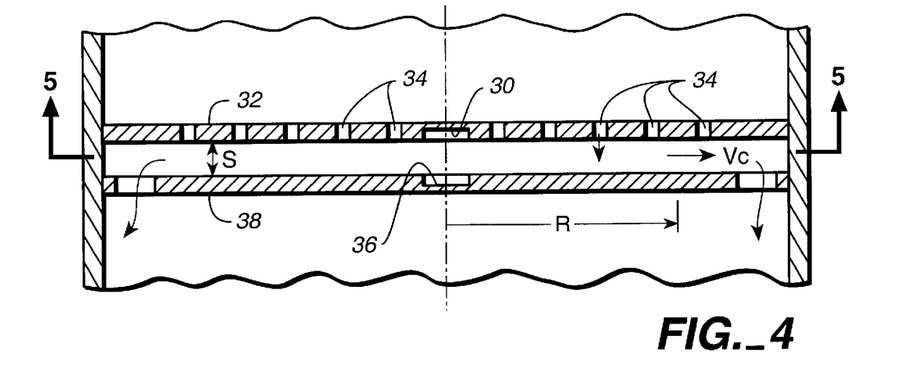
FIG. 4 is a sectional view of a nozzle plate and impaction plate illustrating the structure providing reduction of cross flow embodying the principals of the present invention.
Figure 5:
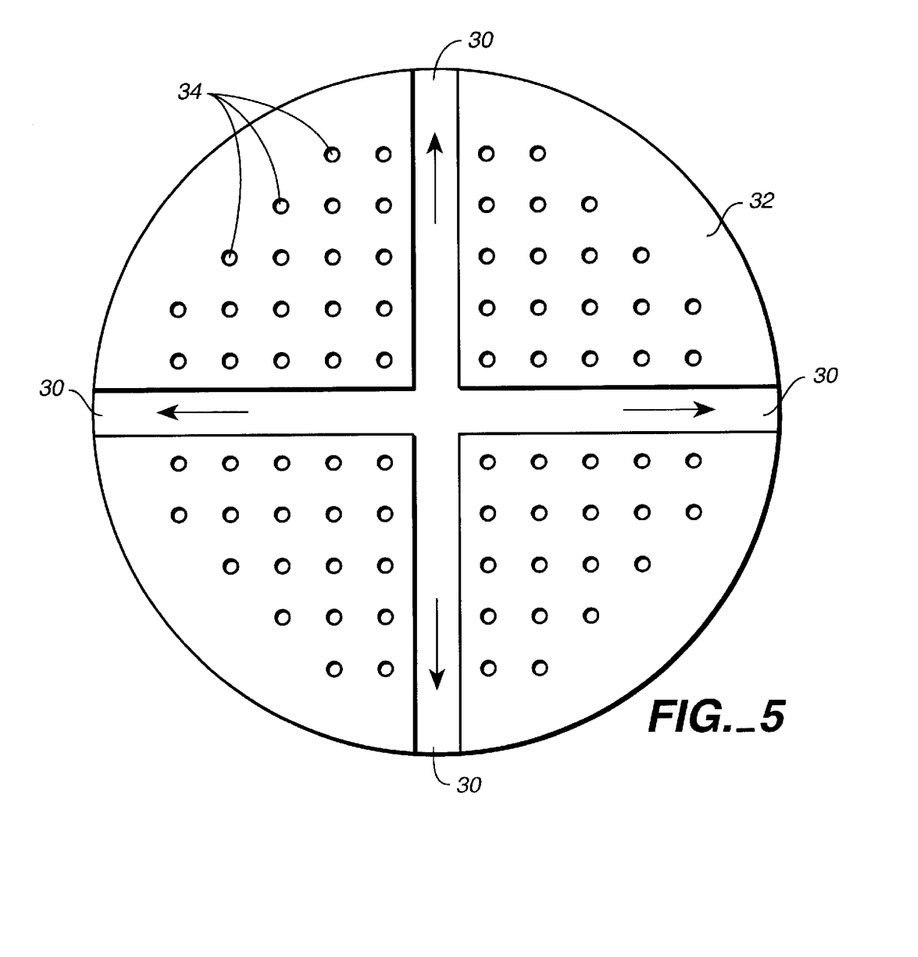
FIG. 5 is a bottom plan view of the nozzle plate of FIG. 4 taken as on line 5—5 in FIG. 4.

One way to reduce the cross-flow effect is to create flow channels or grooves 30 on a nozzle plate 32 and flow channels or grooves 36 on an associated impaction plate 38, as shown in FIGS. 4 and 5 to channel away some of the flow directly to the outside. The outflow reduces the volumetric gas flow through the nozzles 34 of the nozzle plate 32 and the cross-flow velocity experienced by the gas jets near the outer edges of the nozzle cluster, where the cross flow effect is the greatest. The flow channels 30 can be created by simply eliminating one or more rows of nozzles 34 so the flow is along the nozzle plate lower surface without encountering any jets directed toward the impaction plate. Also, grooves 36 can be formed on an impaction plate 38 as shown to increase the cross-sectional area of the channels. In FIGS. 4 and 5, four radial flow channels 30 and 36 are shown, but fewer or more channels can be used depending on the need and the specific nozzle plate design.

Figure 6:
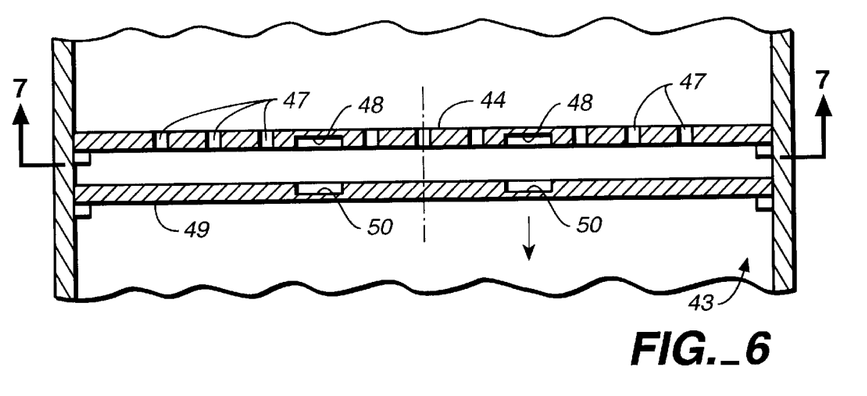
FIG. 6 is a cross sectional view of a modified nozzle plate and impaction plate made according to the present invention for controlling cross flow.
Figure 7:
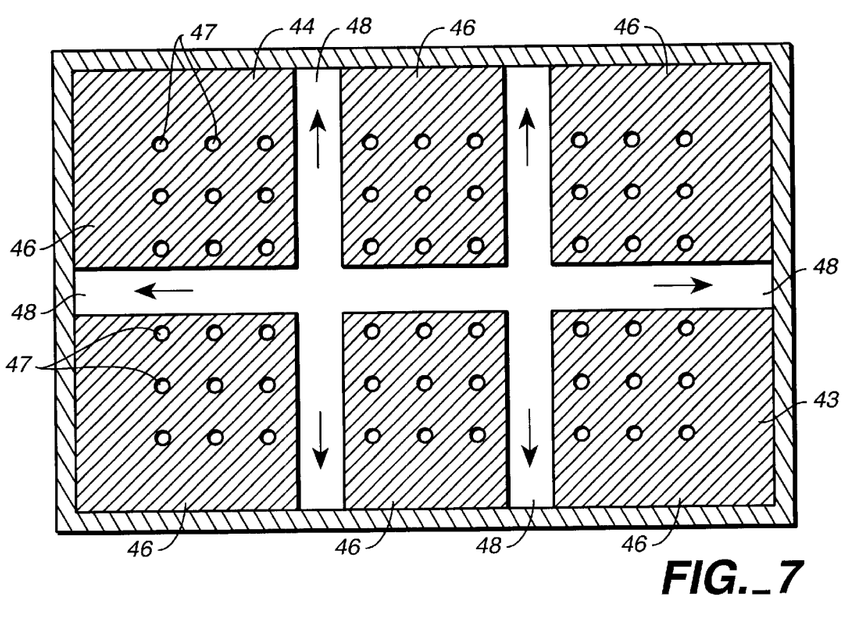
FIG. 7 is a bottom plan view of the nozzle plate of FIG. 6 taken as on line 7—7 in FIG. 6.

The same concept of flow channeling can also be applied to the case of nozzle clusters that are not circular in shape. FIGS. 6 and 7 show an impactor 43 and a rectangular nozzle plate 44 comprised of six square nozzle clusters 46 of nozzles 47 separated by flow channels 48 between the clusters 46. The associated impaction plate 49 also channels 50 underlying channels 48. Using a reasonably small number of nozzles in each cluster makes it possible to investigate in detail the effect of the geometrical arrangement of the nozzles on the overall performance of the nozzle cluster, such as the sharpness-of-cut of the impactor, particle loss characteristics, etc. Once the performance of a cluster 46 of nozzles 47 has been optimized, the cluster can then be replicated at will on the nozzle plate to increase the sampling flow rate of the impactor. Design and development of high performance impactors usually is quite labor intensive. Using optimized nozzle clusters on a nozzle plate, the cost of the development can be reduced and the development time can also be shortened.

Although it is generally preferred to use identical nozzle clusters to produce a high flow rate impactor, the basic concept of flow channeling for controlling cross flow is not restricted to identical nozzle clusters. Various cluster sizes and shapes can be used in an impactor provided the flow from each cluster can be properly channelled away.

In the Micro-Orifice, Uniform Deposition Impactor (MOUDI™) now produced by the MSP Corporation, the uniform deposit feature of the impactor is obtained by using nozzle plates having a substantially uniform distribution of nozzles and rotating the nozzle plates relative to the impaction plates while flow is carried through the nozzles. This rotation causes the particle deposits from the individual nozzles to be spread out uniformly over circular bands on the impaction plates. Using a uniform distribution of nozzles in the nozzle plates, the particle deposit on the impaction plate also becomes substantially uniform. Uniform particle deposit reduces the probability of particle bounce and re-entrainment. It is also demanded by certain chemical analysis techniques, such as X-ray fluorescence.

The rotary motion of the MOUDI™ impactor is achieved by a set of mechanical gears and restraining hooks to produce the relative rotation between the nozzle plate and impaction plate. Such mechanical drive for obtaining rotation has worked satisfactorily, but is not the most ideal or the most flexible. Possible gas leakage in the rotating seals is an issue, and the seals also need to be replaced periodically when they become worn.

Figure 8:
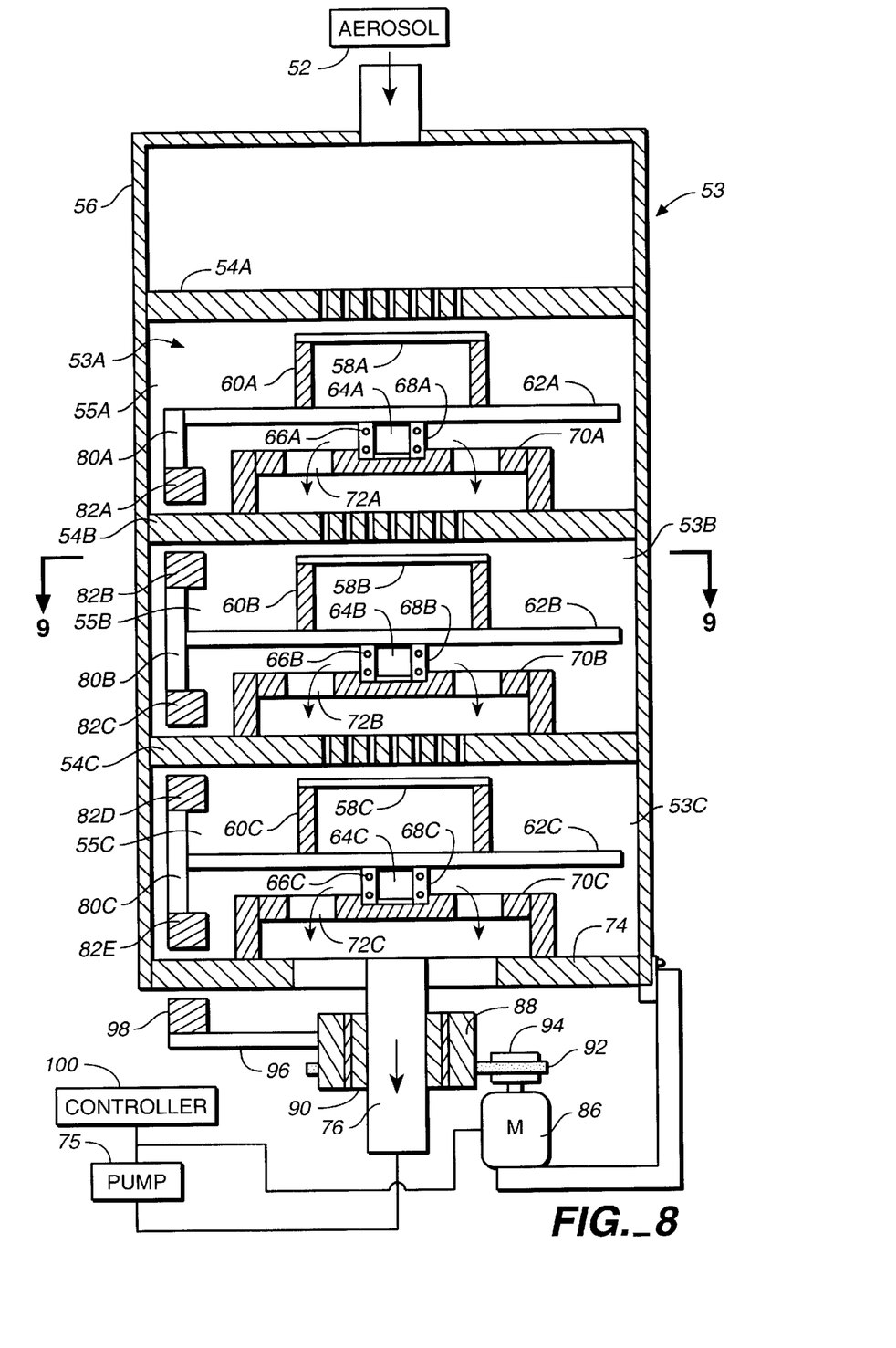
FIG. 8 is a cross sectional schematic representation of a cascade impactor made according to principals of the present invention.
Figure 9:
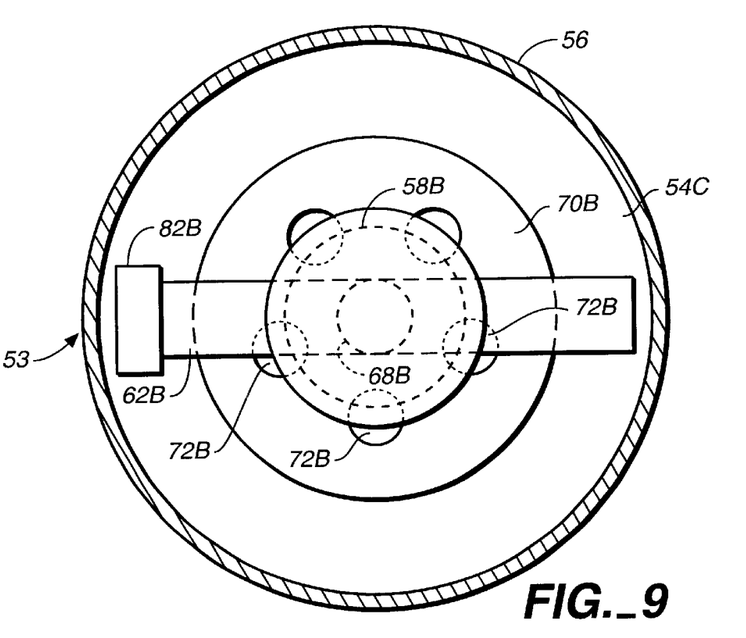
FIG. 9 is a plan view taken on line 9—9 in FIG. 8.

FIG. 8 shows a new structure to produce the relative rotation between each nozzle plate and its associated impaction plate in a cascade impactor. As illustrated in FIG. 8, the cascade impactor 53 is connected to an aerosol source 52 and has impactor stages 53A, 53B and 53C, each with a nozzle plate 54A, 54B and 54C fixed to a support housing 56. Impaction plates, or collection substrates 58A, 58B and 58C are each mounted on a support housing 60A–60C, which can be tubes or open frames. The support housings 60A–60C are mounted on arms 62A–62C that have center mounting shafts 64A–64C that are supported in precision bearings 66A–66C.

The bearings 66A–66C are mounted in bearing housings 68A–68C which in turn are supported on a fixed impaction plate supports 70A–70C, respectively. The impaction plate support includes the horizontal plates with a large number of openings 72A–72C respectively, that do not restrict airflow through the individual cascade impactor chambers that are shown at 55A–55C.

The openings 72A–72C are arranged so that flow through them is substantially unobstructed, and in relation to the nozzles or nozzle openings 53A–53C in each of the nozzle plates 54A–54C, the openings 72A–72C are extremely large.

It is noted that the bearing housing supports 70A and 70B, which also then, in turn, support the impaction plates or collection substrates are mounted at the upper classification or impactor chambers 55A and 55B on the nozzle plates 54B and 54C, respectively, and the lower support 70C is supported on an end plate 74 of the housing 56. The end plate 74 has an airflow outlet tube 76 mounted thereon, as well. The airflow outlet tube is connected to a pump 75. The arms 62A–62C are relatively narrow, so they do not substantially obstruct airflow past them, and as stated are rotatably mounted in precision bearings 66A–66C so there is very little friction resisting rotation. The outer ends of each of the arms 62A–62C have dual magnets attached thereto, and as shown the arm 62A has a depending leg 80A on which a permanent magnet of high strength shown at 82A is mounted. The magnet 82A is spaced from, but is close to the impaction plate 54B that divides the chamber 55A from the chamber 55B.

The arm 62B in chamber 55B has a two section leg 80B attached thereto, with one section of leg 80B extending upwardly from arm 62B and mounting a magnet 82B, and a second section of the leg 80B depending downwardly and mounting a magnet 82C. The magnets 82B and 82C are close to the impaction plates 54B and 54C, respectively as shown, but are spaced from such plates so that they do not interfere with the rotation of the arm 62B, which again, is mounted on very low friction, high precision bearings.

The arm 62C in the chamber 55C of the cascade impactor has a two section leg 80C attached thereto at an outer end, and the leg 80C is similar to the leg 80B in that it extends in upward and downward directions from the arm on which it is mounted. The arm 80C mounts a magnet 82D at the upper end, and another magnet 82E at a lower end. The magnet 82D is close to but spaced from the underside of the nozzle plate 54C and the magnet 82E is spaced above, but close to the end plate 74 of the housing 56.

Since the arms 62A–62C are freely rotatable, the magnets 82A–82E can be used for rotationally driving the arms. In order to provide a magnet drive, a drive motor 86 is mounted, as shown schematically, on the lower side of the end plate 74, and it drives a rotating hub or pulley 88, that is rotatably mounted on the outlet tube 76 using suitable bearings 90. The hub 88 can be a cylinder, driven by a belt 92 from a pulley 94 on the output shaft of the motor 86.

The hub 88 can have a high friction surface so that belt 92 will drive against a cylindrical surface because there is very little load on the hub. The hub is used to mount a radial arm 96, which is fixed to hub 90 and which extends radially from the central axis of the tube 76. The arm 96 is fixed to the hub 90 in a suitable manner. The arm 96 has a drive magnet 98 at its outer end, which is in vertical (radial) alignment with the radial positions of the magnets 82A–83E, and in particular is aligned with the adjacent magnet 82E.

The motor 86 is mounted on a suitable support, to provide clearance for the arm 96 as it rotates, and when the motor 86 is driven under control of a controller 100 the arm 96 will rotate causing the magnet 98 to rotate and because of the orientation of the magnets 98 and magnet 82E, the magnet 82E will be caused to follow the magnet 98 and thus rotate the arm 62C and impaction plate 58C. In turn, the magnet 82D carried on the arm 62C will drive magnet 82C and arm 62B in the chamber 55, thereby rotating the impaction plate 58B. The magnet 82B will drive the magnet 82A in chamber 55A, thereby rotating impaction plate 58A. The magnetic drive is used for rotating the impaction plates underneath the individual nozzles of the respective nozzle plates. The controller 100 also can control the pump 75.

Rotary motion of arm 96 and magnet 98 is transmitted by magnetic coupling between the neighboring magnets and causes all the impaction plates 58A–58C to rotate. The housing 56, which remains stationary, and the nozzle plates, which are also stationary, arms 62A–62C and other components must be made of a non-magnetic material, such as aluminum or plastic, while the magnets 82A–82E are strong permanent magnets. The magnet drive does not require any rotating seals between impaction chambers 55A–55C. Also, different numbers of impactor stages or chambers can be provided with a single motor drive, and there is no need to design or use a different housing for different impactor stages of a cascade impactor. This results in flexibility of use as well as reduced cost of manufacturing.

Figure 10:
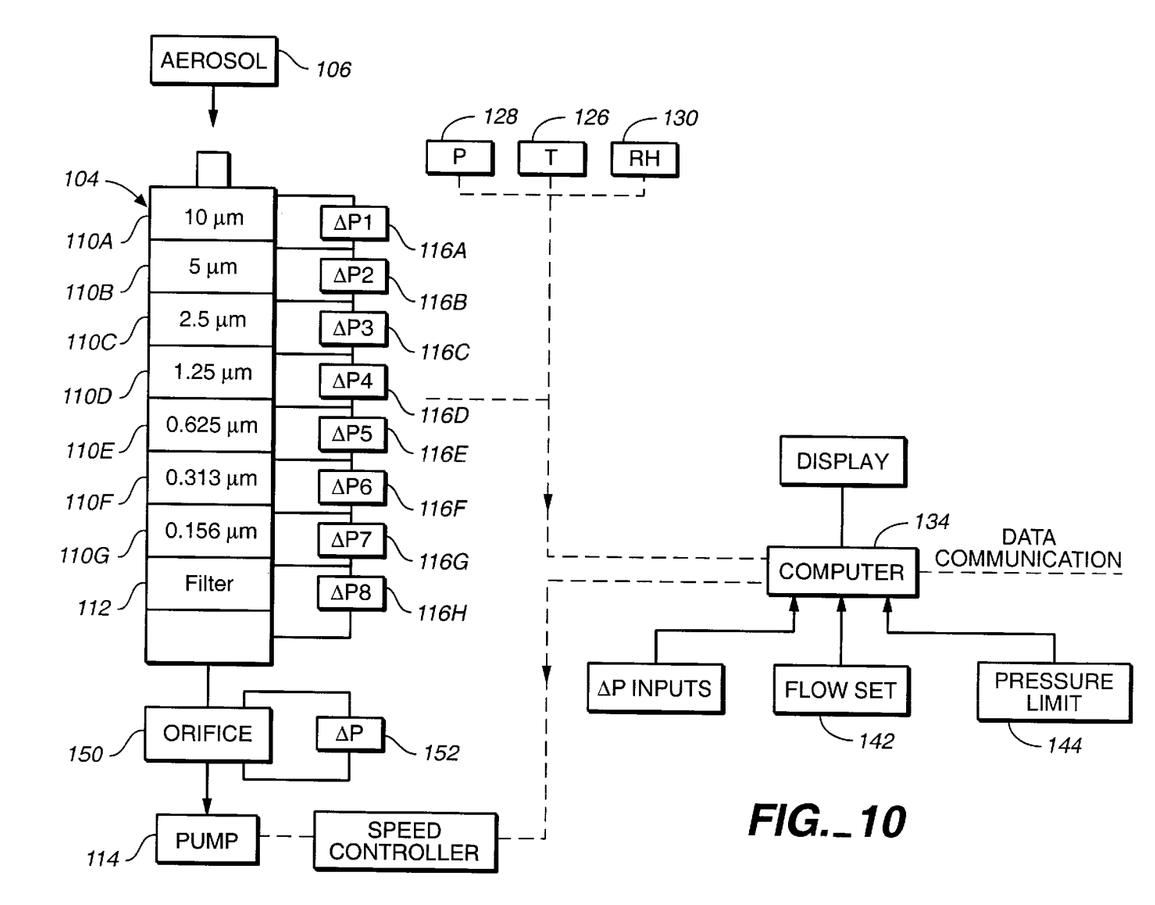
FIG. 10 is a schematic representation of a performance monitoring and control system for cascade impactors made according to the present invention.
Figure 11:
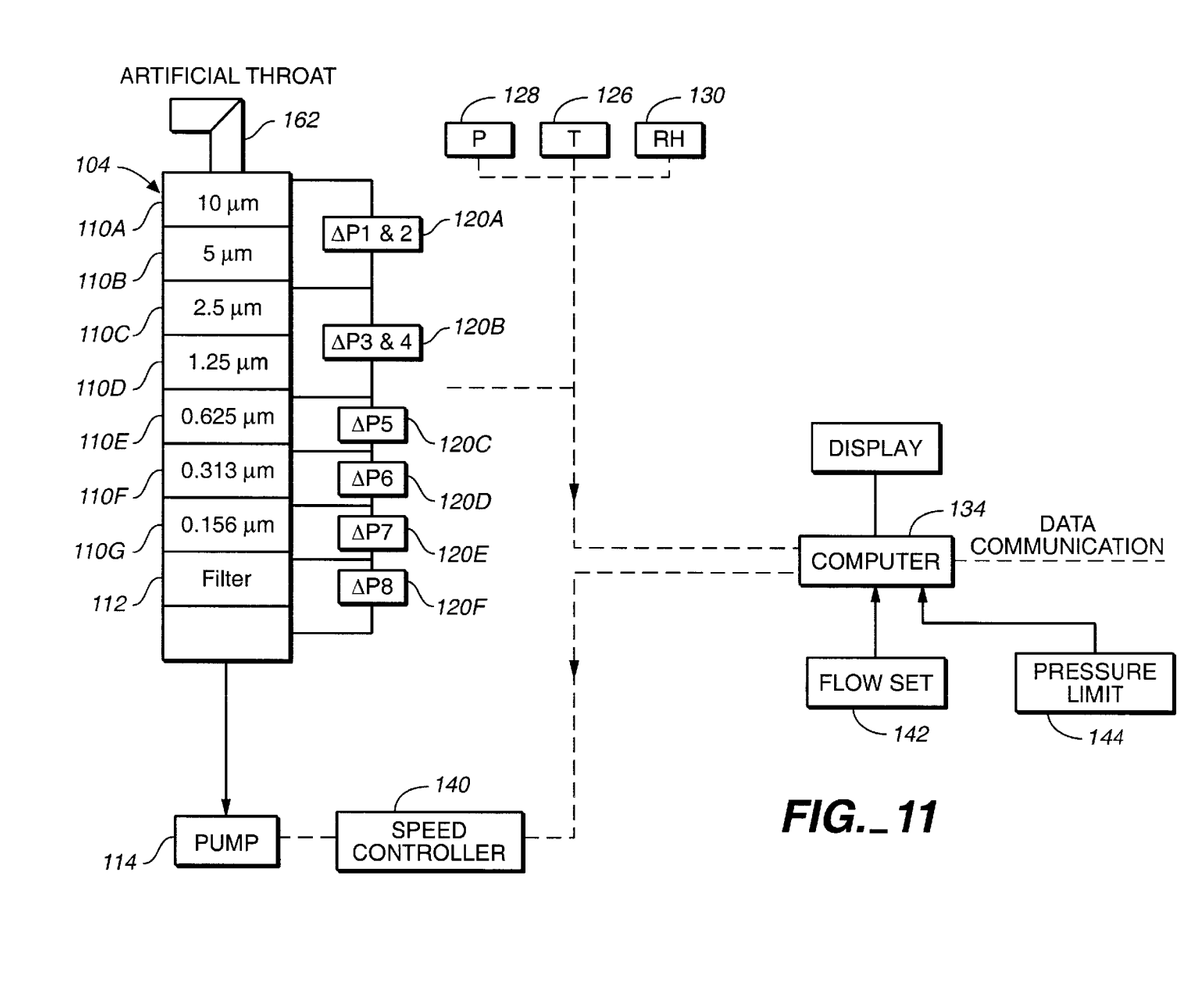
FIG. 11 is a modified form of the monitoring and control system shown in FIG. 6.

FIG. 10 is a schematic diagram of a cascade impactor 104, with impactor stages 110A–110G drawing particle size cutoff points as shown at 10, 5, 25, 1.25, 0.625, 0.313 and 0.156 μm diameter. A filter 112 is used at the outlet. A pump 114 provides the flow of aerosol through the cascade impactor from an aerosol source 106. The pressure differential between adjacent stages is measured by differential pressure sensors 116A–116G are used to measure the pressure drop across each impactor stage. A sensor 116H measures the pressure drop across filter 112. Alternatively, some adjacent impactor stages can be combined and the pressure drop across a group of stages can be measured with a single sensor as shown in FIG. 11.

Figure 12:
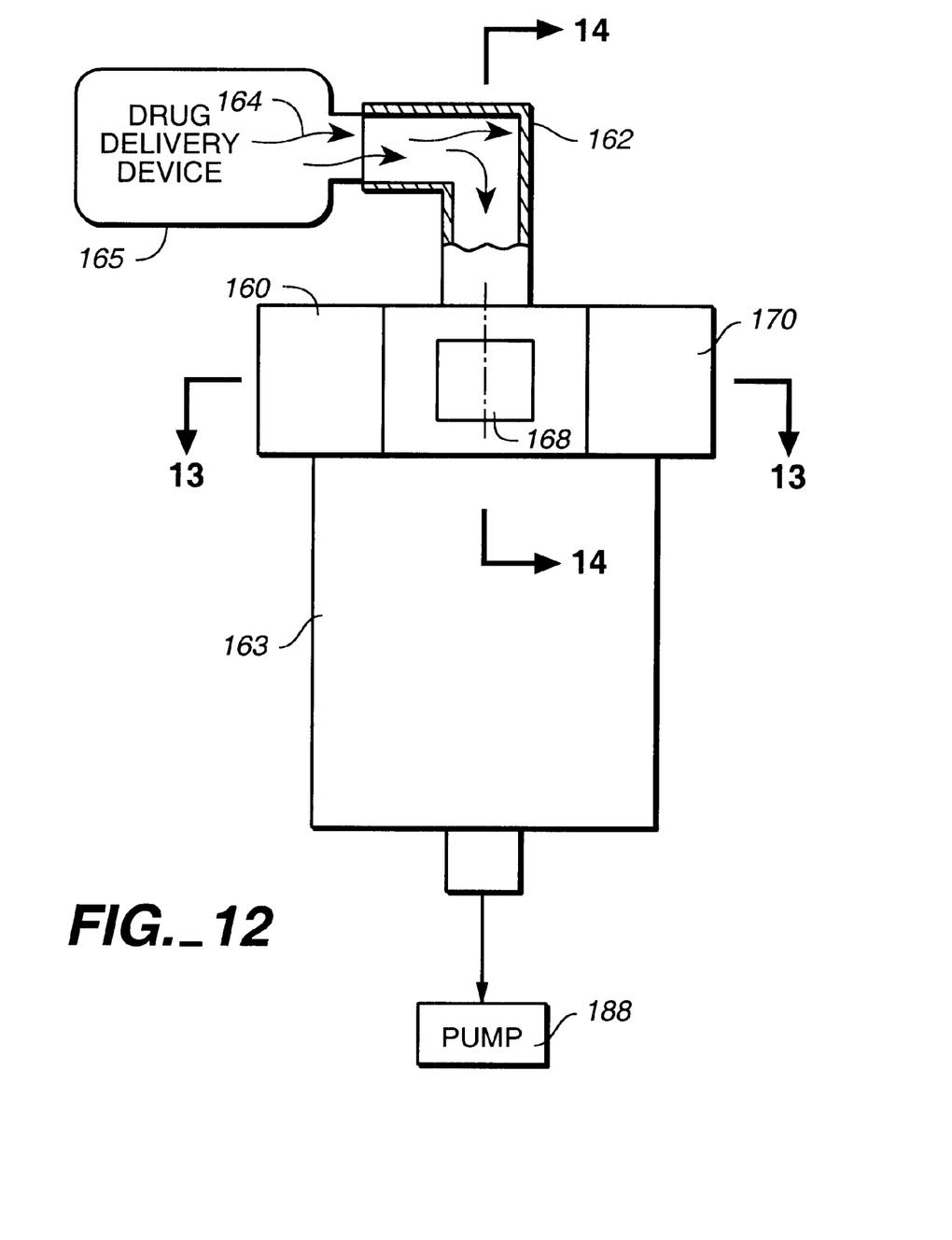
FIG. 12 is a schematic representation of an optical aerosol sensor made according to the present invention.
Figure 13:
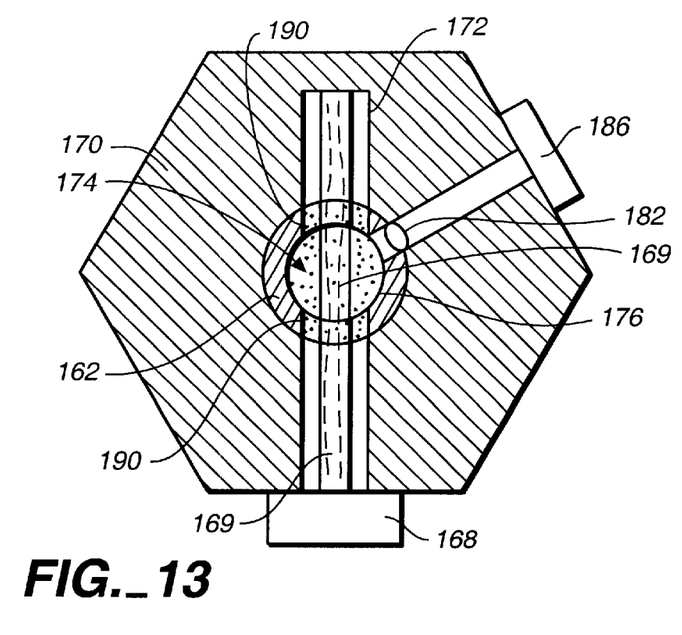
FIG. 13 is a cross sectional view taken on line 13—13 in FIG. 12.
Figure 14:
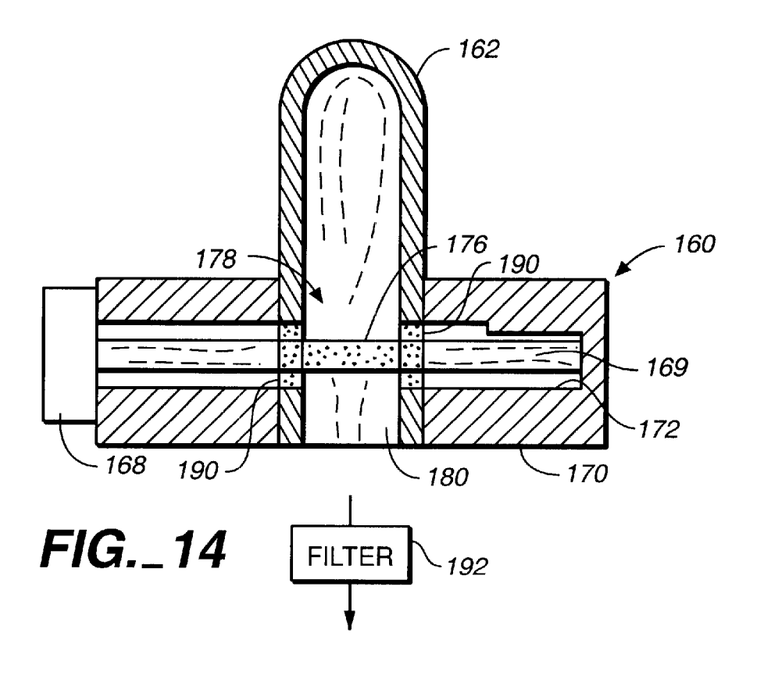
FIG. 14 is a sectional view taken as on line 14—14 in FIG. 12.

The cascade impactor 104 is the same as that shown in FIG. 10, but in this instance, the impactor inlet is an artificial throat formed as a USP Inlet described more fully in connection with FIGS. 12, 13 and 14. The pressure sensors shown at 120A, 120B, 120C, 120D, 120E and 120F are arranged differently so that the sensor 120A is used to measure the pressure drop across two stages. As shown, stages 110A and 110B, and the pressure sensor 120B, are used for measuring the pressure drop across stages 110C and 110D. The sensors 120C, 120D, 120E and 120F again are used for sensing the individual pressure drops across stages 110E, 110F and 110G, and the filter 112.

This reduces the number of pressure sensors needed, hence, the cost of the overall system. Ambient temperature can be sensed with a temperature sensor 126. Barometer pressure is sensed with a sensor 128; relative humidity can be sensed with a sensor 130. Flow rate can be sensed by calculating the flow based on measured pressure drop across an orifice plate. A separate flow sensor can be used. The sensors are connected to a computer 134 for signal processing and recording. The computer 134 can also generate an electrical signal based on the sensor inputs to adjust the flow by controlling the speed of pump 114 (or 75) with a speed controller 140 to one of several preset values.

The pressure drop across each impactor stage can be sensed by the individual pressure sensors and compared with standard or reference values which may be obtained by calibration at the factory or at user's standard calibration laboratory at periodic intervals.

During use in the field, when particles begin to accumulate on the small nozzles in the nozzle plates, the pressure drop across the nozzle plate increases. This increase can be detected. In addition, any leak in the system, damage to the nozzle plates due to cleaning or other causes, as well as a mistake in the assembly and operation of the impactor can also be detected automatically.

Preset pressure limits can also be established so that when the pressure difference between the measured value during use and the calibrated set point exceeds the limit, the operator will be alerted to the situation for corrective actions. The data can also be stored in the computer memory from a flow set control 142 and a pressure limit controller 144. Each pressure sensor can be individually monitored by the computer. This way, changes that have occurred during sampling can be detected and the time at which these changes have taken place will also be known. This will enable the experimenter to determine if the data are sufficiently accurate for use or need to be discarded.

Change in nozzle opening dimensions due to particle accumulation and blockage is generally not an issue when the nozzle is a few millimeter or more in diameter. For smaller nozzles, especially those found in modern precision impactors such as the MOUDI™ impactor mentioned earlier, it is important. Due to the very small nozzle diameter, the nozzle plate carrying these small nozzles must also be very thin, typically a few thousandth of an inch in thickness. Such thin nozzle plates can be easily damaged during ultrasonic cleaning. Presently, there is no convenient way of detecting the small change in nozzle diameter due to particle accumulation and/or damage during cleaning. Manual inspection by microscope is slow and labor intensive. Due to the high microscope magnification needed to see the small nozzles, the field of view is quite small, meaning that only a few nozzles can be seen and examined in a given field of view. Since micro-orifice nozzle plates with as many as 2,000 nozzles are routinely made, and as many as 10,000 nozzles may be needed in the future, the convenient and low cost method of detecting change in nozzle dimensions is described above accomplishes the objective automatically.

One of the most important causes of inaccurate or invalid data is operator error. Since cascade impactor stages each have a separate nozzle plate, they can be assembled incorrectly and in the wrong sequence. Leakage in O-ring and other types of seals used in a cascade impactor can also cause invalid data to be generated. The method described above can detect both of these problems automatically and at low cost.

One further advantage of sensing the pressure drop across the impactor stages is that the flow through a cascade impactor is often maintained by the use of a critical flow control orifice. The critical orifice shown at 150 in FIG. 10 is a small diameter orifice through which a constant gas flow is maintained by the vacuum pump 114. When the pressure downstream of the orifice is below about half of the upstream pressure, as sensed by a differential pressure sensor 152, the flow becomes sonic at the orifice. The flow then becomes choked. Changes in the downstream pressure then does not affect the volumetric or mass rate of gas flow through the orifice, as long as the downstream pressure is smaller than about half of the upstream pressure.

A critical flow orifice 150 (FIG. 10) is a very convenient way of maintaining a constant flow through a device, such as a cascade impactor. However, such small critical orifices can also be clogged by metal chips and burrs left from machining. A change in orifice diameter will produce a change in flow rate and there is no convenient way of measuring this flow in a cascade impactor. If a flow meter is inserted at the inlet to the cascade impactor, it will cause particle loss at the inlet, reduce the quantity and size distribution of the aerosol being collected by the cascade impactor downstream and results in an error in measurement. Locating a flow meter downstream of the final filter in the cascade impactor where the pressure may be substantially below the ambient atmospheric pressure will require corrections to take into account the volumetric expansion of the gas. In the present invention, one of the impactor stages can be used as a flow metering stage since it is connected to a pressure transducer and its pressure drop is measured. For use as a flow meter, the specific impactor stage must have a nozzle diameter that is sufficiently large so that the nozzle clogging is unlikely to occur. The nozzle diameter must be sufficiently small to cause a pressure drop that is high enough so that it is easily measurable with accuracy. This way, the expense of an additional flow meter can be avoid and the technical difficulty of where to locate the flow meter is also absent. Thus, an early stage, near the flow inlet is used.

Studies show that to be suitable for use as a flow-metering stage, the nozzle diameter in a nozzle plate must be larger than about 0.3 mm in diameter. Nozzles smaller than 0.3 mm in diameter have the possibility of being partially clogged during operation due to particle accumulation around the edges of the nozzles near the entrance, thereby changing their effective opening size and hence the pressure drop. For the same reason, only nozzles smaller than 0.3 mm diameter need to be monitored to detect area changes due to particle accumulation, since large nozzles are unlikely to be clogged by particles deposition at the nozzle entrance.

Pressure drop monitoring provides a very sensitive way of monitoring changes in nozzle diameters. According to theory, the cut-point diameter of an impactor stage is determined by the dimensionless Stokes number defined as:

$$St = \frac{u\tau}{D}$$

where u is the gas flow velocity through the nozzle, τ is the particle relaxation time, and D is the nozzle diameter. For a specific nozzle design, the value of the St is fixed. The above equation can then be used to determine how changes in nozzle flow velocity, u, and nozzle diameter, D, can affect the particle relaxation time. The particle relaxation time is a function of particle size and the gas properties. For a specific gas, such as air, the gas properties are fixed, and the relaxation time then depends only on particle size. Hence, the equation can be used to determine the effect or changes in u and D on the size of particle the impactor can collect by impaction.

To estimate the effect of dimension changes, it should be noted that a 1% reduction in nozzle diameter, D, would cause a 2% reduction in nozzle area. With the same volumetric gas flow through the nozzle, the velocity will then increase by 2%. The pressure drop will then increase by 4% based on the Bernoulli' law. Since the particle relaxation time depends on the second power of particle diameter, the cut-point diameter of the nozzle will then decrease by 1.5%. Thus, by monitoring the pressure drop across nozzle plate, a 4% change in pressure drop will correspond to an impactor cut-point change of only 1.5%. Since pressure drop changes of 1% or less can be relatively easily measured with a precision pressure transducer, cut-point diameter changes of 0.4% or smaller can be easily detected. For a 50 $\mu$m diameter nozzle, 0.4% change in diameter corresponds to a 0.2 $\mu$m change in actual dimension. Such a small change in diameter cannot be easily measured with available optical inspection tools.

Pressure drop monitoring, therefore, is most effective by choosing a nozzle plate having larger than 0.3 mm diameter nozzles as a flow metering stage, and then monitoring the pressure drop of nozzle plates with nozzles smaller than 0.3 mm for effects of particle accumulation. This way, inaccurate flow measurement as well as nozzle clogging can be simultaneously detected with confidence by pressure drop monitoring across nozzle plates.

One important application of cascade impactors is to measure the size distribution of aerosols produced for medicinal uses. In such applications, the specific chemical compound, i.e. drug, is aerosolized, which is then inhaled by the patient. The most widely used devices for producing medicinal aerosols for inhalation therapy are the metered dose inhaler (MDI) and the dry-powder inhaler (DPI). These devices produce a specific quantity of drug in aerosol form with each application, usually by depressing the device with a thumb or squeezing the device between fingers to release a puff of aerosol containing the required dose which the patient then inhales.

It is important to know both the dose, and the size distribution of aerosols produced by these devices. The aerosol size distribution is important because it determines how much and where the aerosol will deposit in the patient's respiratory system. Particles in the 3-to-10 $\mu$m range will usually deposit in the upper respiratory airways, i.e. the trachea and the bronchial airways, while smaller particles will penetrate more deeply into the lung and be deposited in the alveolar region. For instance, bronchial dilating drugs for treating asthma generally require a significant portion, if not the major portion, of the drug aerosol to be in the 3 to 10 $\mu$m range for the drug to be effectively delivered to the target site.

The operating characteristics of a MDI or a DPI is usually determined by sampling the medicinal aerosol into a cascade impactor and analyzing the quantity of aerosol collected in each impactor stage to determine both the size distribution and the total aerosol output. The impactor performance monitoring system shown in FIGS. 10 and 11 will insure that the performance of the impactor has not changed during use, the small nozzles have not been partially plugged, no leakage has occurred, or that the impactor stages have been assembly correctly. The performance-monitoring device will insure high data quality and greatly reduce the labor involved in record keeping and report preparation.

The stable operation of a specific type of MDI or DPI is very important to insure consistent output in total dose and size distribution. An aerosol-sensing device that can sense one or more of the aerosol characteristics automatically will be a valuable tool in the design and development of MDI and DPI and quality assurance in production.

FIG. 12 is the schematic diagram of an optical aerosol sensor 160 that can be used for this purpose. The device consists of an optical aerosol sensor fitted with a standard USP Inlet 162, which is an angular tubular piece made of two circular tubes joined at a right angle. The USP Inlet 162 is a standard inlet described in the U.S. Pharmacopoeia 23, published by U.S. Pharmacopoeal Convention, Rockville, Md. It has well-defined physical dimensions to simulate particle impaction in the human throat. When the output aerosol from a MDI or a DPI (delivery device 165) is directed at the USP Inlet, as shown by arrow 164, large particles will be removed by the device 164 imparting on the back wall in a manner similar to that of the human throat. With the use of the USP Inlet 162, the optical aerosol sensor 160 will sense only aerosol particles capable of entering the human respiratory system.

The rapid response of the optical aerosol sensor 160 makes it possible to determine the time profile of drug delivery by the MDI or DPI. The optical sensor can also be used without the USP Inlet for other applications for simultaneously sensing the aerosol concentration by optical means with optical sensor 160 while collecting the aerosol with a cascade impactor 163 at the outlet of the optical sensor or filter sampler for size distribution or total mass analyses. The collected particle sample can also be analyzed chemically to determine the medicinal content of the collected particles.

For purpose of illustration, the optical aerosol sensor is shown in more detail in FIGS. 13 and 14. A light source 168, preferably a solid-state laser, projects a collimated beam of light 169, into a cavity 172 comprising light trap in the housing 170. The cavity 172, is coated with a light absorbing material to prevent reflection and back-scattering. The aerosol cloud 174 is shown flowing through the circular passageway 176 between the inlet 178 and outlet 180 of the optical sensor 160. The aerosol in the path of the light beam 169 is illuminated and scatters light. A lens 182 (FIG. 13) collects a fraction of the scattered light reflected from the aerosol in the viewing volume 184 into a photo-detector 186. As the puff or cloud 174 of aerosol released by the MDI and DPI is carried by the steady flow of gas passing through the optical sensor and provided by a vacuum pump 188. The sensor output from photodetector 186 will rise and fall in proportion to the rise and fall in aerosol concentration in the viewing volume. By this means, the time profile of drug delivered by a specific MDI or DPI can be measured, while the aerosol is being collected with the cascade impactor shown at 163 or a filter 192 shown in FIG. 14 for size distribution or total mass analysis.

For MDI and DPI testing, aerosol particles deposited on the inside walls of the USP Inlet must be recovered and analyzed as part of the total aerosol output of the MDI or DPI. This is usually accomplished by rinsing the interior surface of the USP Inlet 162 with an appropriate solvent, such as distilled water. The solvent can then be analyzed chemically to determine its medicinal content. To facilitate this process, a transparent window and lens 190 can be formed into the walls of the inlet, making them integral parts of the Inlet. This way, the deposited material on the window can be recovered in the usual manner by removing the window and lens. At the same time the windows and lens can be cleaned each time after use.

An important application of the optical aerosol sensor and particle collector is to measure the dose uniformity of drug delivery devices such as the MDI and the DPI. For this application, the particle collector would be a filter (FIG. 14), and the device can be used with or without the USP Inlet. In the procedure currently used for testing such devices, as described in the U.S. Pharmacopoeia, the dose is measured by directing the aerosol cloud onto a filter, which is then analyzed. In a 100-dose device, i.e., a device capable of producing 100 doses, 10 separate dose samples are collected and individually analyzed. The values are then averaged to give the so-called "label-claim dosage." In this procedure, the remaining 90 doses are wasted. The procedure is laborious and time consuming. It also measures the average dose based on statistical sampling, rather than the entire content of the device.

In the present invention, the light scattering aerosol sensor measures particle concentration in the aerosol cloud as it passes through the laser beam on its way to the filter. The particle scattered light signal can be integrated with respect to time and compared with the actual mass of particles collected by the filter to provide a calibration for aerosol mass. Once calibrated, the device can be used to measure the mass output of a drug delivery device on each dose produced by the device.

To perform a dose-uniformity test, the MDI or DPI is attached to the inlet of the aerosol sensor. Each time a dose is released, the scattered light signal is obtained and stored in the computer, which then analyzes the signal to obtain an integrated scattered light value to obtain the dose. The actual dose is also collected by the filter. After the entire content of the device has been emptied following the release of 100 doses on a 100-dose device, the filter is then analyzed. The total quantity of material collected by the filter divided by the number of doses produced is then the true average dose. The dose uniformity is obtained by analyzing the stored data in the computer. This procedure requires only the analysis of one filter sample, as opposed to the 10 samples currently required by U.S. Pharmacopoeia. It is also more accurate, because the entire content of the device has been collected and analyzed.

The optical sensor shown in FIGS. 13 and 14 is one of several ways aerosol particles can be sensed optically. Other approaches include the use of light transmission, as opposed to light scattering, for particle sensing. The scattered or transmitted light can also be sensed by a charge-coupled device (CCD) similar to those used in digital still and video cameras. These and other methods of optical aerosol sensing will be obvious to those skilled in the art. They can all be used in the unique and novel combination described in this invention where a USP Inlet 162 is used in combination with an optical sensor 160, and a cascade impactor 163 or a filter to simultaneous sense and collect medicinal aerosols for analysis.

Although the present invention has been described with reference to preferred embodiments, workers skilled in the art will recognize that changes may be made in form and detail without departing from the spirit and scope of the invention.

What is claimed is:

1. A particle classifier comprising a housing containing a plurality of individual classification stages, each classification stage classifying different size particles, said housing having a gas inlet and a gas outlet, a flow controller to maintain a gas flow from the gas inlet to the gas outlet at a desired value, each classification stage comprising a nozzle plate, each nozzle plate having a plurality of nozzles of substantially the same size and shape, which are different from the size and shape of the nozzles of other nozzle plates, one of the nozzle plates comprising nozzles sized to provide a flow metering stage, the gas flow passing through the flow metering stage nozzle plate and the other nozzle plates of classification stages in series flow, a first pressure transducer connected to measure the differential pressure across the one nozzle plate for determining the flow therethrough and a second differential pressure transducer for measuring the differential pressure across at least one additional nozzle plate for determining the operating condition of the at least one additional nozzle plate.

2. The particle classifier of claim 1 further comprising a comparator to compare the differential pressure measured by the pressure transducer connected across the one nozzle plate comprising the flow metering stage and having nozzles larger than 0.3 mm in diameter with a reference pressure at a desired flow rate, and to provide an output.

3. The particle classifier of claim 2 wherein there is a pressure transducer connected to measure the differential pressure across a classification stage nozzle plate having nozzle diameters smaller than 0.3 mm, and the differential pressure measured by the pressure transducer is recorded in the memory of a computer.

4. The particle classifier of claim 2 further comprising a source of gas flow, the flow controller being connected to control the gas flow rate from the source of gas flow through the housing to a selected desired value to operate the particle classifier at a desired flow rate.

5. The particle classifier of claim 1, wherein the pressure transducer comprises a differential pressure sensor having a pair of pressure inlets, and providing the differential in pressures between the inlets, a first of said inlets having a fitting for fitting to a first impactor stage on a first side of a nozzle plate, and a second of said inlets having a fitting for fitting to the same impactor stage on an opposite side of said at least one nozzle plate.

6. The particle classifier of claim 5 and an output from said sensor indicating a differential between pressures on opposite sides of the at least one nozzle plate.

7. The particle classifier of claim 1, wherein the at least one nozzle plate has nozzles smaller than 0.3 mm.

8. The particle classifier of claim 1 further comprising a plurality of impaction plates, each impaction plate aligned with an associated nozzle plate of the classification stages to form an impaction stage, said impaction plates each being substantially parallel to and spaced from the associated nozzle plate.

9. The particle classifier of claim 1, wherein the nozzles of the flow metering stage have a diameter greater than 0.3 mm.

10. The particle classifier of claim 1, wherein the nozzles of at least one of the classification stages have a diameter less than 0.3 mm.

11. A particle classifier comprising a housing containing a plurality of individual classification stages, said housing having a gas inlet and a gas outlet, a flow controller to maintain a gas flow from the gas inlet to the gas outlet at a desired value, each classification stage comprising a nozzle plate having a plurality of nozzles of a different size from nozzles of other nozzle plates, the gas flow passing through the classification stages in series flow, a pressure transducer connected to measure the differential pressure across at least one nozzle plate for determining the operating condition of the at least one nozzle plate, wherein the flow controller includes a computer, a temperature sensor connected to measure ambient temperature, and a pressure sensor to measure barometric pressure, the computer calculating a flow rate from the flow controller based on the measured temperature, barometric pressure, and the differential pressure sensed by connecting the pressure transducer across said at least one nozzle plate, said at least one nozzle plate containing nozzles larger than 0.3 mm in diameter, and providing an electrical signal to set the flow rate to a specific set point value.

13. The particle classifier of claim 11 wherein a pump is connected to provide the gas flow from the inlet to the outlet, and the flow controller comprises an orifice carrying the gas flow and connected to the particle classifier to maintain a constant gas flow rate through the particle classifier.

13. A particle classifier comprising:

a housing, said housing having a gas inlet and a gas outlet;

a flow metering stage in the housing;

a plurality of individual classification stages, said flow metering stage and said classification stages each comprising a nozzle plate having a plurality of nozzles of substantially the same size and shape, wherein the nozzles of the flow metering stage have a diameter greater than 0.3 mm. and the nozzles of at least one of the classification stages have a diameter less than 0.3 mm.;

a flow controller to maintain a gas flow at a desired value, the gas flow passing through the flow metering stage and the classification stages in series flow; and a pressure transducer connected to measure the differential pressure across at least one nozzle plate for determining the operating condition of the at least one nozzle plate.

\* \* \* \* \*